United States Patent [19]

Chuen

[11] Patent Number: 5,385,471
[45] Date of Patent: Jan. 31, 1995

[54] CEREC INLAY HOLDER AND INSERTER

[76] Inventor: Ng T. Chuen, Flat A, 28th Floor, Shing Loong Court, 13 Dragon Terrace, Causeway Bay, Hong Kong

[21] Appl. No.: 175,210

[22] Filed: Dec. 27, 1993

Related U.S. Application Data

[63] Continuation-in-part of Ser. No. 698, Jan. 5, 1993, abandoned.

[51] Int. Cl.⁶ .................. A61C 3/00; B25B 7/00; B25B 9/00
[52] U.S. Cl. .................. 433/153; 433/157; 433/158; 433/161; 433/162; 606/210; 294/99.2
[58] Field of Search .............. 433/153, 157, 158, 161, 433/162; 606/205, 210, 133; 294/99.2; D28/55

[56] References Cited

U.S. PATENT DOCUMENTS

| | | | |
|---|---|---|---|
| D. 157,104 | 1/1950 | Tuttle et al. | D28/55 |
| 1,133,334 | 3/1915 | Strycker | 294/99.2 X |
| 1,177,706 | 4/1916 | Johnson | 433/161 |
| 2,685,880 | 8/1954 | Curutchet | 294/99.2 X |
| 3,306,139 | 2/1967 | Brackett | 294/99.2 |
| 4,506,669 | 3/1985 | Blake, III | 294/99.2 X |
| 5,308,357 | 5/1994 | Lichtman | 606/205 |

FOREIGN PATENT DOCUMENTS

| | | | |
|---|---|---|---|
| 2610501 | 8/1988 | France | 294/99.2 |
| 537945 | 11/1931 | Germany | 606/211 |
| 0101275 | 9/1923 | Switzerland | 606/211 |

*Primary Examiner*—Paul J. Hirsch
*Assistant Examiner*—Nicholas D. Lucchesi
*Attorney, Agent, or Firm*—Samuels, Gauthier & Stevens

[57] ABSTRACT

A dental instrument comprising a grasping device in the form of a tweezer member having a finger receiving ring detachably connected to one of the legs of the tweezer member is disclosed. The instrument is used for holding and inserting a Cerec inlay, manufactured by a dental Cerec machine, in a tooth undergoing a restorative procedure. The instrument may further include a threaded axle which coacts with each leg of the tweezers and protrudes from one of the legs. The instrument may also further include a plunger mechanism which facilitates the insertion of an inlay in a prepared tooth cavity.

28 Claims, 7 Drawing Sheets

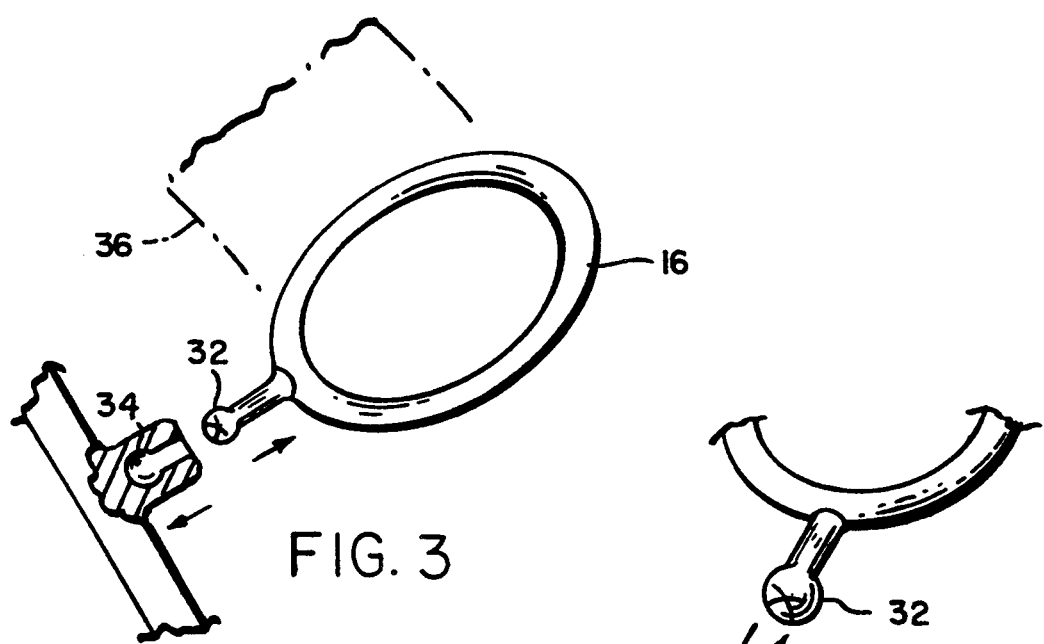
FIG. 3
FIG. 4
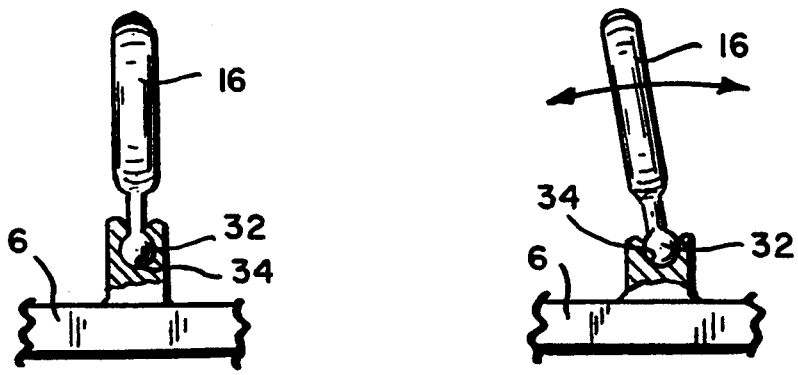
FIG. 5
FIG. 6

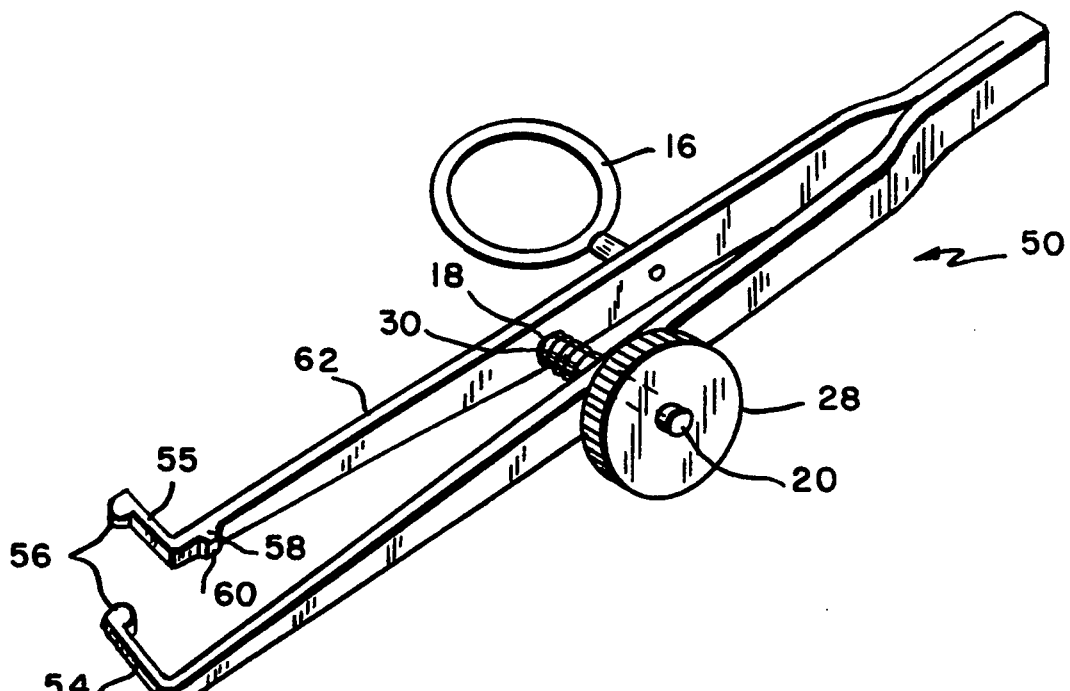
FIG. 14
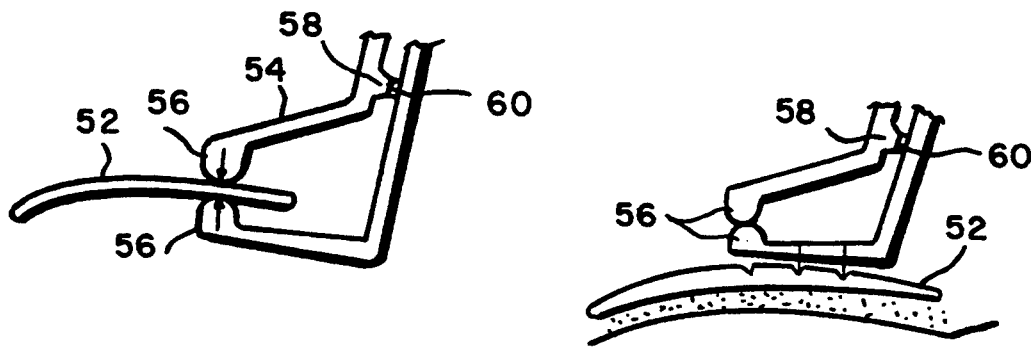
FIG. 15
FIG. 16

CEREC INLAY HOLDER AND INSERTER

BACKGROUND OF THE INVENTION

This is a continuation-in-part of U.S. patent application Ser. No. 08/000,698 filed on Jan. 5, 1993, entitled "CEREC INLAY HOLDER AND INSERTER", now abandoned.

FIELD OF THE INVENTION

This invention relates generally to dental instruments and is concerned in particular with a Cerec inlay holder and inserter for holding and inserting a Cerec inlay manufactured by a dental Cerec machine.

DESCRIPTION OF THE INVENTION

Cerec inlays are used to restore teeth to their natural tooth translucency. The inlays are made using Cerec machines which utilize computer aided means to design a Cerec inlay to match a person's existing teeth. A copy of a brochure issued by Siemens was filed in the parent application and the original brochure was filed on May 20, 1991 under patent application 9110894.4.

Traditionally, there have been difficulties in handling Cerec inlays with conventional tweezers, namely because the Cerec inlays are relatively small, typically the size of a few cubic millimeters and thus are easily dropped. Also, it is awkward to maneuver the inlay during the long and complicated process of preparing the Cerec inlay in the milling chamber of the Cerec machine through the time that the inlay is cemented to the oral cavity. The Cerec inlay can become contaminated with saliva, especially when the Cerec inlay is placed into the posterior region of the mouth. The Cerec inlay holder and inserter of the present invention is designed to overcome these difficulties and to provide a dental instrument so that the Cerec inlay can be handled with precision.

SUMMARY OF THE INVENTION

The primary objective of the present invention is to provide an inexpensive Cerec inlay holder and inserter which can be used to hold and insert a Cerec inlay with precision. By using the Cerec inlay holder and inserter of the present invention, the risk of accidentally dropping the Cerec inlay is greatly reduced.

According to the present invention there is provided a Cerec inlay holder and inserter which includes tweezers having two legs which extend from a common base and wherein contra-angled gripping segments are disposed at the distal ends of the legs. The Cerec inlay holder and inserter may further include a finger support which may be detachably connected to one of the legs of the tweezers. The finger support comprises a cross-cut ball which fits into a socket located on the tweezers to form a male/female lock. Once attached, the finger support is able to rotate 360° and tilt up to 50° to facilitate easy maneuvering. One advantage of the finger support is that the ring portion of the device may come in a wide variety of ring sizes to fit many different finger sizes. It also allows many different users to comfortably maneuver the device.

The Cerec inlay holder and inserter may further include a threaded axle which coacts with each leg of the tweezers and protrudes from one of the legs. A semi-spherical screw cover is positioned at the end of the protruding axle. A wheel knob located on the protruding portion of the threaded axle is capable of forward and backward rotational movement along the threaded axle.

The Cerec inlay holder and inserter may further include a plunger mechanism. The plunger mechanism is used to facilitate the removal of a Cerec inlay which is being held by the device.

BRIEF DESCRIPTION OF THE DRAWINGS

FIG. 3 illustrates the detachable finger support and the socket on one leg of the tweezers;

FIG. 4 further illustrates the cross-cut ball and socket of the present invention;

FIG. 5 illustrates the ball and socket device permitting rotation;

FIG. 6 shows the ball and socket device permitting tilting;

FIG. 14 is a perspective view of a holder and inserter having gripping segments used to hold and insert an anterior veneer;

FIG. 15 illustrates the holder and inserter of FIG. 14 grasping an anterior veneer;

FIG. 16 illustrates the holder and inserter of FIG. 14 placing an anterior veneer in position;

DETAILED DESCRIPTION OF THE ILLUSTRATED EMBODIMENT(S)

Figure 1:
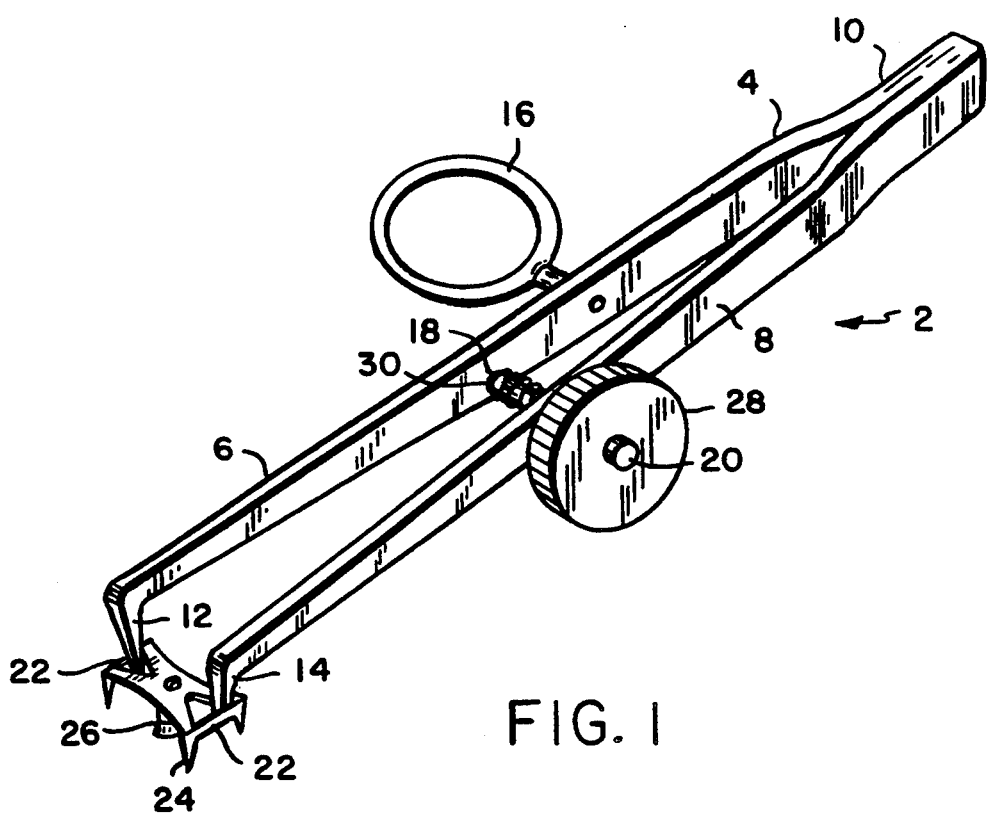
FIG. 1 is a perspective drawing of a Cerec inlay holder and inserter in accordance with the present invention.

With reference to the drawings the grasping device, or specifically the Cerec inlay holder and inserter, in accordance with the present invention is generally indicated at 2 in FIG. 1. The grasping device 2 includes a tweezer 4 having two legs 6, 8 which extend from a common base 10. Located at the end of the two legs are gripping segments 12 and 14 which are contra-angled. A finger support, specifically a finger receiving ring, 16 is detachably connected to leg 6. A threaded axle 18 coacts between each of the legs 6 and 8 and protrudes through leg 8. A semi-spherical screw cover 20 is located at the end of the axle to prevent an injury caused by the protruding threaded axle. One embodiment of the present invention which includes branched crosspieces 22 having four claws 24 extended therefrom and a plunging mechanism 26 located therebetween.

Figure 2:
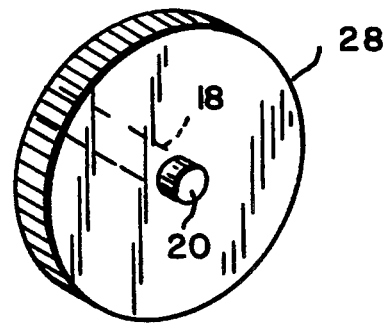
FIG. 2 shows the semi-spherical screw cover and wheel knob of FIG. 1.
Figure 7:
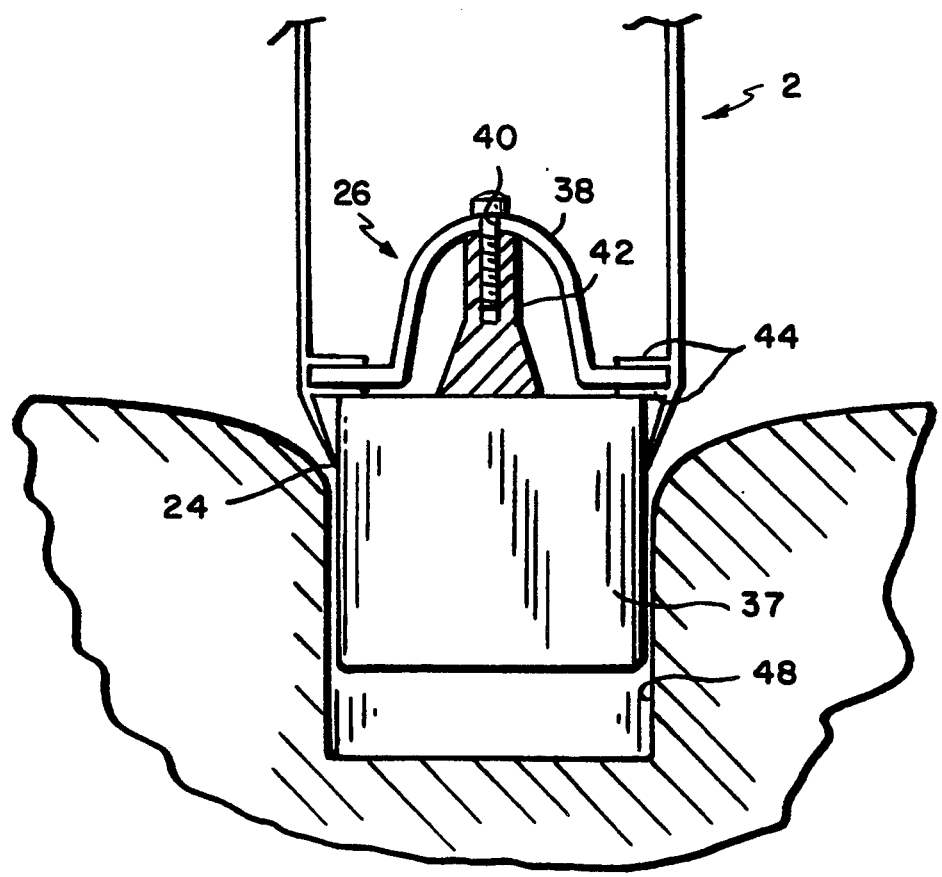
FIG. 7 is a side view of the gripping segments of the tweezers which includes a plunger mechanism.

The threaded axle 18 is connected to the inner portion of leg 6 and protrudes through to the outer side of leg 8. As seen in FIGS. 1 and 2, the end of the axle is covered with a semispherical screw cover 20 to prevent accidental trauma of tissue. A wheel knob 28 is positioned on the portion of the threaded axle protruding through leg 8. The wheel knob 28 is capable of forward and backward rotation along the threaded axle 18 for the purpose of increasing and decreasing the distances between the gripping segments 12, 14. The wheel knob 28 can be adjusted to manipulate the claws 24 closer together to create a hard or soft grip on the object which the grasping device 2 is to pick up and hold. When the object which is being held is to be released, the wheel knob 28 will be rotated in the opposite direction to increase the distance between the claws 24 and thus release the object being held. Furthermore, the portion of the threaded axle located between the legs may have a spring 30 surrounding the threaded axle 18 to assist in the open and closing of the claws 24.

FIGS. 3 through 6 further illustrate the detachable finger receiving ring 16 which is detachably connected to leg 6. FIGS. 3 and 4 illustrate the finger receiving ring 16 having a ball 32 which is cross-cut for positioning in socket 34 to form a male/female lock. FIG. 5 illustrates the finger receiving ring 16 positioned in the socket 34 so that the ring is permitted to rotate 360° and FIG. 6 illustrates the ring 16 positioned in the socket 34, such that the ring is permitted to tilt up to 50°, both to facilitate easy maneuvering.

When using the grasping device 2, the user slides a finger (not shown), usually the index finger, through the finger receiving ring 16. The finger receiving ring 16 comes in many different sizes and is detachably connected to the grasping device 2 for many different reasons, including different dentists having different ring sizes; some portions of a procedure are done by the dentist while other portions are done by a nurse and thus the device can be passed from one person to the other often while still grasping an object; and different portions of the procedure require different tools and hence the finger receiving ring 16 can be detached from one tool and reattached to another tool without having to slide a finger 36 from the finger receiving ring 16.

By employing a finger receiving ring 16 as disclosed herein, a person using the grasping device 2 may continue gripping the device without the necessity of the other fingers of the hand. This frees the other fingers, especially the thumb, to adjust the wheel knob 28 and thus the distance between the gripping segments of the grasping device so that a second hand is not required to either pick up or release an object leaving the other hand free to do other things related to the procedure, i.e. hold the mouth open.

For a left-handed dentist, the threaded axle 18, wheel knob 28 and the finger receiving ring 16 can be placed in the inverse position on the grasping device 2.

Figure 10:
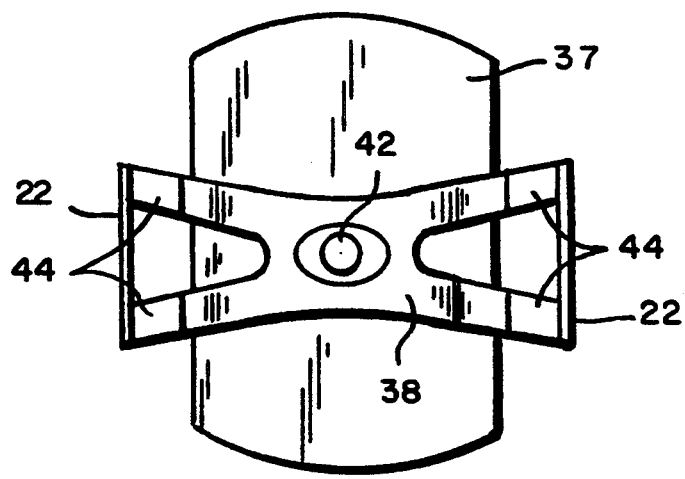
FIG. 10 is top view of the plunging mechanism of FIG. 9.
Figure 11:
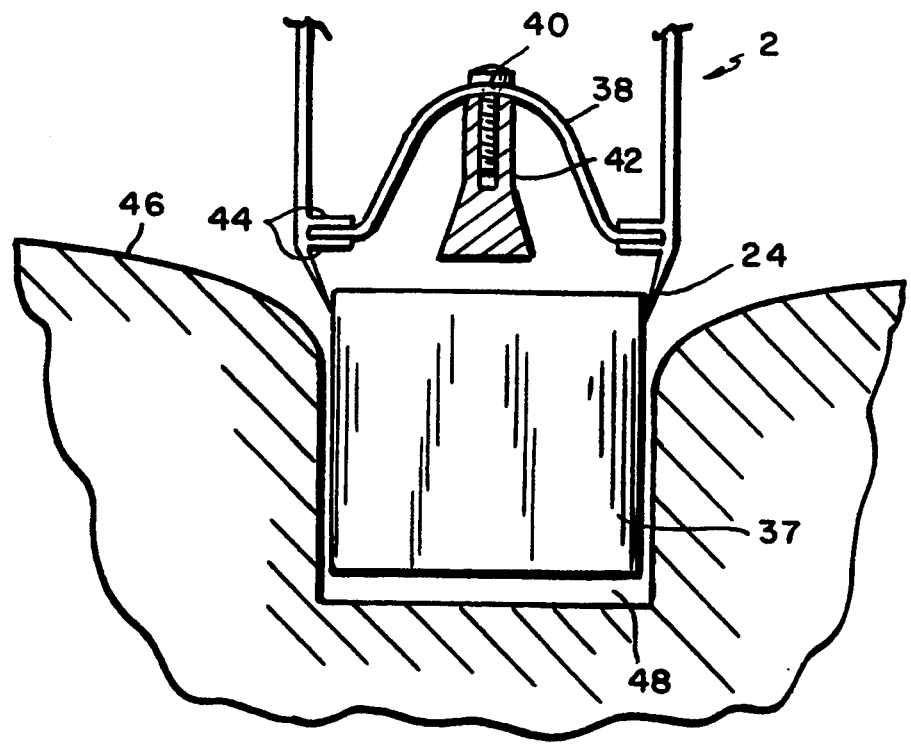
FIG. 11 is a side view of the insert layer and holder which is about to remove a Cerec inlay from a mouth.
Figure 12:
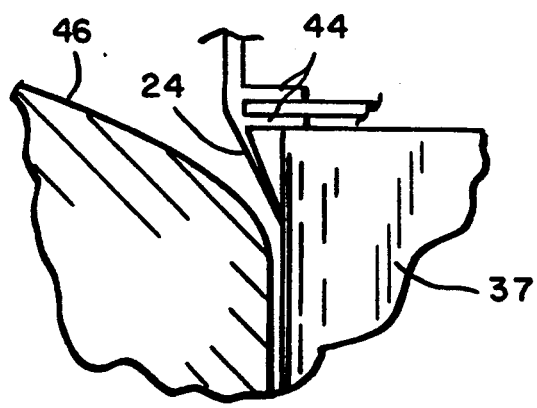
FIG. 12 illustrates the contact points between a Cerec inlay and the gripping segments of the present invention.
Figure 13:
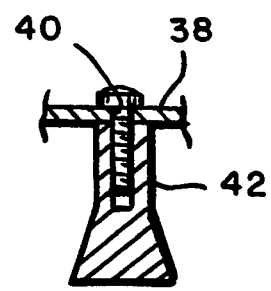
FIG. 13 illustrates the screw portion of the plunging mechanism which is positioned in the hole of the cross-shaped band.

As can be seen in FIGS. 7–11, the grasping device 2 may further comprise a plunging mechanism 26 which can be used to help release a Cerec inlay 37 from the grasping device and insert it into place. The plunging mechanism 26 includes a thick cross-shaped elastic stainless steel band 38 having a hole 40 disposed in the center thereof. A screw 42 passes through the hole and is secured in place. The cross-shaped elastic stainless steel band 38 is attached to the branched shanks 22 with flat occlusal stoppers 44. The occlusal stoppers 44 at the ends of the cross-shaped band 38 act as stabilizers against upward movement of a Cerec inlay 37 as can best be seen in FIG. 7. The claws 24 extend laterally downwards from the branched shanks 22 and incline at an angle similar to that of a cusp 46 of a tooth 47 as there will be little space between the cusp 46 and the lateral wall of the Cerec inlay 37 as shown by FIG. 12. The claws 24 are sharp and pointed for the purpose of creating a firm grip with minimal contact with the Cerec inlay 37, thus maximizing exposure of the Cerec inlay 37 surface for chemical dipping and rinsing.

Figure 8:
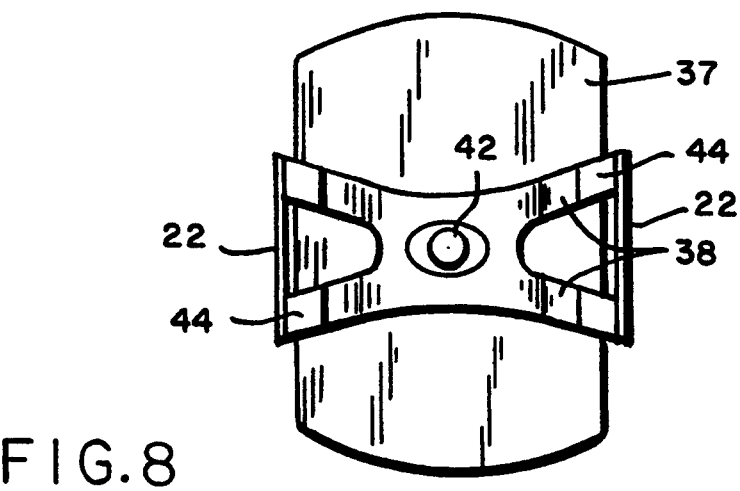
FIG. 8 is a top view of the plunger mechanism in which the Cerec inlay holder and inserter is grasping a Cerec inlay.

The grasping device 2 can be used to hold the Cerec inlay 37 by putting a finger (not shown), usually the index finger, through the finger receiving ring 16 and coupling the finger receiving ring 16 to the leg 6 of the grasping device 2. By holding the grasping device 2 in this fashion, the other fingers of the hand are free to adjust the distance between the claws 24 by controlling the wheel knob 28 until the claws 24 are in contact with the Cerec inlay 37. The four claws 24 and the four sets of occlusal stoppers 44 provide eight points of contact, four of which are illustrated in the side view of FIG. 7. The cross-shaped elastic stainless steel band 38 is under tension while the grasping device is holding a Cerec inlay 37. FIG. 8 shows the plunging mechanism 26 from the top, under tension, while holding the Cerec inlay 37.

Figure 9:
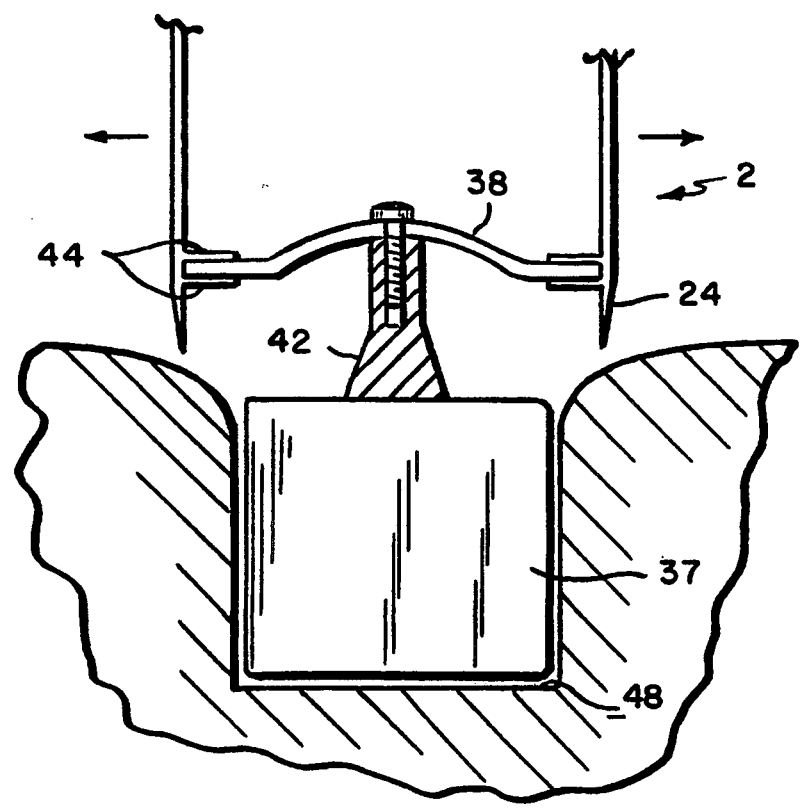
FIG. 9 is a side view of the plunging mechanism pushing the Cerec inlay from the Cerec inlay inserter and holder.

To insert the Cerec inlay 37 in position, the control knob 28 is adjusted with one finger to increase the distance between the claws 24. As the distance between the claws 24 is increased, the tension of the cross-shaped band 38 is released so that the band begins to flatten, thus forcing the screw 42 downward to push the Cerec inlay 37 into a cavity 48 as shown in FIGS. 9 and 10.

The grasping device can also be used to recover a Cerec inlay 37. The pointed sharp lateral claws 24 act as an initial gripping aid in recovering the deep seeded Cerec inlay 37 as illustrated in FIG. 11. Throughout all of the processes previously described, the grasping device 2 is easily operated by only one hand so that the other hand of the user is free to carry on related procedures.

When the grasping device 2 is holding a Cerec inlay 37, the gripping segments have been designed to allow for maximum exposure of the Cerec inlay 37. This is important in a variety of related procedures including dipping the Cerec inlay 37 in chemicals and then rinsing it. The gripping segments have been designed to avoid side extensions on a Cerec inlay or to avoid a burr on the Cerec inlay so that the burr can be trimmed. The firm grip of the grasping device can withstand the vibration caused by trimming so that the Cerec inlay will not be dropped during this process. Also, the grasping device can be used to repeatedly insert and withdraw a Cerec inlay from a cavity lined by thin articulating paper. This process can be used to determine if there are high spots in the inlay and so that the inlay can be further ground before being permanently placed in position.

FIG. 14 illustrates a grasping device 50 used to hold anterior veneers 52. The gripping segments 54, 55 are each at different angles and lengths and have semispherical grips 56 at the ends thereof which are used to prevent scratching of the anterior veneer 52 surface. Also shown in FIG. 14 is a dead space stopper 58 having a rubber cushion pressure absorber 60 on the end thereof. This gripping device 50 works in the same method as the earlier described device used to hold Cerec inlays 37; however, it has now been modified to hold anterior veneers 52 which are curved as indicated in FIGS. 15 and 16. The dead space stopper 58 is used to prevent overexertion of force when adjusting the wheel knob 28 such that when the dead space stopper 54 reaches the opposing leg, the user will no longer be able to adjust the wheel knob and shorten the distance between the two gripping segments 54, 55.

Figure 17:
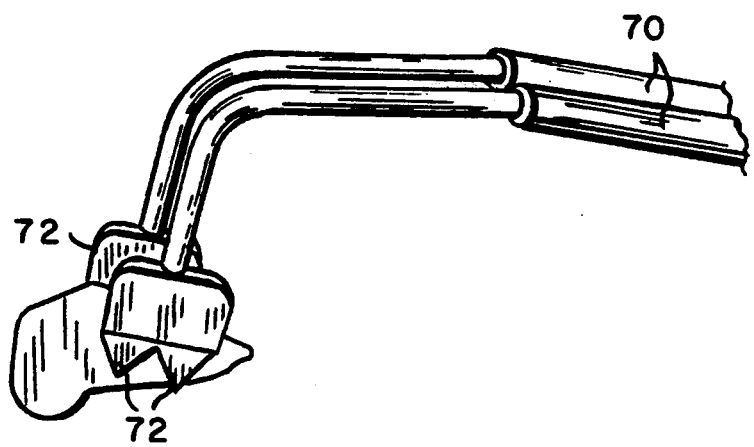
FIG. 17 is a side view of the gripping segments of an alternate of the present invention.
Figure 18:
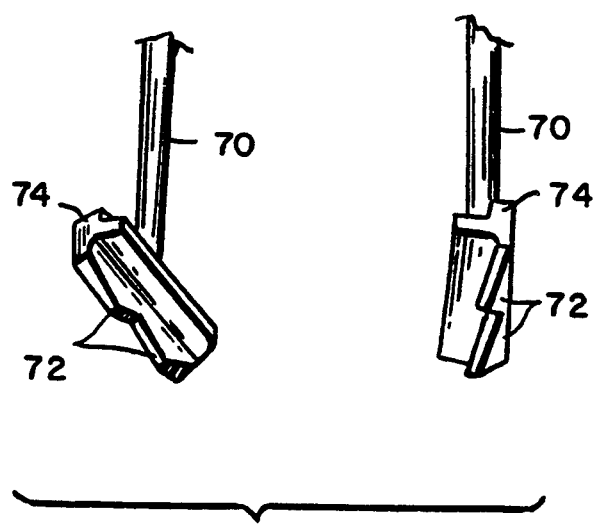
FIG. 18 is a front view of the gripping segments of FIG. 16.

The present invention has been described with two different sets of gripping segments and end portions thereof. FIGS. 17 and 18 disclose an alternative embodiment of the present invention and illustrate a grasping device 70 having four claws 72 and a shoulder 74 to hold the Cerec inlay 37 in place and keep it from upward movement.

In light of the foregoing, it will now be appreciated by those skilled in the art that the present invention provides a novel dentistry tool which incorporates a detachably connectable finger receiving ring which can be used so that the remaining fingers of the hand grasping the device can adjust the distance between the gripping segments of the grasping device. While the present device has been described in connection with specifically shaped gripping segments and claws and in the field of dentistry, it should be noted that the detachable finger receiving ring with or without the adjustment mechanism can be used with other instruments used to pick up and hold components such as those having soft cushions on the ends of the gripping segments to pick up odd shaped items, to pick up minute computer components or even grasping devices to pick up insects and small animals. The gripping segments can be straight, diverging, converging, square, or circular to accommodate whatever component is desired to be grasped.

The foregoing description has been set forth primarily to illustrate the invention and is not intended to be limiting. Since modifications of the described embodiments incorporated in the spirit and substance of the invention may occur to persons skilled in the art, the scope of the invention should be limited solely with reference to the appended claims and equivalents.

What is now claimed is:

1. A grasping device comprising:
   a tweezer member having a pair of mutually spaced legs extending resiliently from a common base and terminating at their distal ends in cooperatively arranged gripping segments;
   means defining a socket extending laterally from one of said legs;
   a finger receiving ring; and
   connecting means protruding from said ring, said connecting means being removable from and insertable in said socket to thereby accommodate attachment and removal of said ring to and from said tweezer member.

2. The grasping device of claim 1, wherein said finger receiving ring can rotate 360° and tilt up to 50° when attached to said tweezer member.

3. The grasping device of claim 2, further comprising: an adjustment mechanism coacting with each of the legs of said tweezer member to adjust the distance between said gripping segments.

4. The grasping device of claim 3, which further comprises
   a threaded axle disposed between each of said legs and wherein said threaded axle protrudes from the other of said legs; and
   a knob capable of forward and backward movement along said threaded axle such that said knob rotates to adjust the distance between said gripping segments, said knob is provided on the portion of said threaded axle protruding from said other leg.

5. The grasping device of claim 4, wherein said gripping segments of said tweezer member are contraangled.

6. The grasping device of claim 5, wherein attached to said gripping segments are crosspieces having gripping claws extending therefrom.

7. The grasping device of claim 6, which further comprises plunger means for expelling components held by said grasping device.

8. The grasping device of claim 7, wherein said plunger means includes a cross-shaped band attached to said crosspieces, said cross-shaped band having a hole disposed in the center of said band and a rod adapted to fit in said hole.

9. The grasping device of claim 8, wherein said rod is a screw.

10. The grasping device of claim 8, wherein said band is held in place with flat occlusal stoppers.

11. The grasping device of claim 4, wherein said tweezer member has two unequal length gripping segments, each curving upwards at a different angle.

12. The grasping device of claim 1, wherein said connecting means protruding from said ring includes a cross-cut ball.

13. A grasping device comprising:
   a tweezer member having a pair of mutually spaced legs extending resiliently from a common base and terminating at their distal ends in cooperatively arranged gripping segments;
   an adjustment mechanism coacting with each of said legs to adjust the distance between said gripping segments;
   a finger receiving ring detachably connected to one of said legs; and means for detachably connecting said finger receiving ring to said tweezer member.

14. The grasping device of claim 13, wherein said adjustment mechanism. Further comprises:
   a threaded axle disposed between each of said legs of said tweezer member and wherein said threaded axle protrudes from the other of said legs; and
   a knob capable of forward and backward movement along said threaded axle such that said knob rotates to adjust the distance between said gripping segments, said knob is provided on the portion of the threaded axle protruding from the tweezer member.

15. The grasping device of claim 14, wherein a semispherical cover is disposed at the end of said threaded axle.

16. The grasping device of claim 15, which further comprises plunger means for expelling components held by the grasping device.

17. The grasping device of claim 13, wherein said gripping segments of said tweezer member are contraangled.

18. The grasping device of claim 17, wherein said tweezer member has two unequal length gripping segments, each curving upwards at a different angle.

19. The grasping device of claim 13, wherein said grasping device further includes a socket extending laterally from one of said legs, and wherein said finger receiving ring includes connecting means protruding from said ring, said connecting means being removable from and insertable in said socket to thereby accommodate attachment and removal of said ring to and from said tweezer member.

20. The grasping device of claim 19, wherein said finger receiving ring can rotate 360° and tilt up to 50° when attached to said socket.

21. A grasping device comprising:

a tweezer member having a pair of mutually spaced unequal length legs extending resiliently from a common base and terminating at their distal ends in cooperatively arranged gripping segments, said gripping segments extending upward each at a different angle;

a threaded axle;

a knob capable of forward and backward movement along said threaded axle such that said knob rotates to adjust the distance between said gripping segments;

a detachable finger receiving ring; and means for detachably connecting said finger receiving ring to said tweezer member.

22. The grasping device of claim 21, wherein said means for detachably connecting said finger receiving ring to said tweezer member includes a socket extending laterally from one of said legs, and wherein said finger receiving ring includes connecting means protruding from said ring, said connecting means being removable in said socket to thereby accommodate attachment and removal of said ring to and from said tweezer member.

23. The grasping device of claim 22, wherein said finger receiving ring can rotate 360° and tilt up to 50° when attached to said socket.

24. The grasping device of claim 22, wherein a semi-spherical cover is disposed at the end of said threaded axle.

25. A grasping device comprising:

a tweezer member having a pair of mutually spaced unequal length legs extending resiliently from a common base and terminating at their distal ends in cooperatively arranged gripping segments, said gripping segments extending upward each at a different angle;

semi-spherical clenching segments disposed at the ends of the gripping segments;

a threaded axle;

a knob capable of forward and backward movement along said threaded axle such that the knob can be rotated to adjust the distance between said gripping segments;

a detachable finger receiving ring and means for detachably connecting said finger receiving ring to said tweezer member; and means for determining the amount of pressure that can be applied to said tweezer member when said tweezer member is grasping a component.

26. A grasping device of claim 25, wherein said means for determining the amount of pressure that can be applied to said tweezer member includes a dead space stopper having a rubber cushion pressure absorber on the end of said stopper.

27. The grasping device of claim 25, wherein the means for detachably connecting said finger receiving ring to said tweezer member includes a socket extending laterally from one of said legs, and wherein said finger receiving ring includes connecting means protruding from said ring, said connecting means being removable from and insertable in said socket to thereby accommodate attachment and removal of said ring to and from said tweezer member.

28. The grasping device of claim 27, wherein said finger receiving ring can rotate 360° and tilt up to 50° when attached to said socket.

* * * * *